(12) United States Patent
Talati et al.

(10) Patent No.: US 10,172,348 B2
(45) Date of Patent: Jan. 8, 2019

(54) LOW TOXICITY COMPOSITION

(71) Applicant: UPL LTD., Haldia (IN)

(72) Inventors: Paresh Vithaldas Talati, Haldia (IN); Jaidev Rajnikant Shroff, Dubai (AE); Vikram Rajnikant Shroff, Dubai (AE)

(73) Assignee: UPL LTD., Haldia, West Bengal (IN)

( * ) Notice: Subject to any disclaimer, the term of this patent is extended or adjusted under 35 U.S.C. 154(b) by 0 days.

(21) Appl. No.: 15/482,515

(22) Filed: Apr. 7, 2017

(65) Prior Publication Data

US 2018/0000072 A1    Jan. 4, 2018

(51) Int. Cl.
| | |
|---|---|
| *A01N 25/32* | (2006.01) |
| *A01N 25/12* | (2006.01) |
| *A01N 37/08* | (2006.01) |
| *A01N 43/40* | (2006.01) |
| *A01N 53/00* | (2006.01) |

(52) U.S. Cl.
CPC ............. *A01N 25/32* (2013.01); *A01N 25/12* (2013.01); *A01N 37/08* (2013.01); *A01N 43/40* (2013.01); *A01N 53/00* (2013.01)

(58) Field of Classification Search
CPC ........ A01N 25/32; A01N 25/12; A01N 53/00; A01N 37/08
See application file for complete search history.

(56) References Cited

U.S. PATENT DOCUMENTS

| | | | | |
|---|---|---|---|---|
| 6,444,618 | B1 * | 9/2002 | Aven ...................... | A01N 25/02 504/317 |
| 2008/0096763 | A1 * | 4/2008 | Dawson ................. | A01N 25/30 504/206 |

FOREIGN PATENT DOCUMENTS

| | | |
|---|---|---|
| EP | 1349456 B1 | 12/2005 |
| EP | 1585389 B1 | 3/2011 |
| EP | 1701616 B1 | 12/2011 |
| WO | 2006008614 A2 | 1/2006 |
| WO | 2014152980 A1 | 9/2014 |

OTHER PUBLICATIONS

Watano et al., Powder Technology, 2003;131:250-255.*
Falkowitz et al.; (abstract 091); 2017 American College of Medical Toxicology (ACMT) Annual Scientific Meeting; J Med Toxicol Mar. 2017; 13(1): 3-46. Published online Feb. 23, 2017. doi: 10.1007/s13181-017-0599-3).
Mikron Insecticide_product information from Transport_ 18 pages_ (2012); http://www.globalexterminating.com/wp-content/uploads/2014/03/Transport-Mikron-Ins-09-28-12-Comm.pdf.
Safety Data Sheet Transport Mikron Insecticide from FMC, SDS# 6549-A, Version 1.05; 9 pages; (2017); https://www.rosepestsolutions.com/docs/msds/Transport-Mikron-SDS-2017.pdf.

* cited by examiner

*Primary Examiner* — San Ming R Hui
(74) *Attorney, Agent, or Firm* — Cantor Colburn LLP

(57) ABSTRACT

The invention provides a composition comprising a) Acetamiprid, b) Bifenthrin and c) a toxicity control agent. The invention also provides a method for preparing the composition as well as a method for controlling insects and acarids using the composition.

9 Claims, No Drawings

LOW TOXICITY COMPOSITION

FIELD OF INVENTION

The present invention relates to a composition comprising acetamiprid, bifenthrin and a toxicity control agent. The invention also relates to a method for preparing the composition as well as a method for controlling insects and acarids using the composition.

BACKGROUND

Insecticidal activity of nicotinyl compounds is well known. Pyrethroids are known to be active against acarids such as ticks and mites. For a broader pesticidal activity or for enhanced activity of one of the actives, such compounds are often used in combination. EP1349456 discloses a combination of nicotinyl compound and pyrethroid for the control of insects and acarids. WO2006008614 discloses a synergistic insecticidal composition comprising chloronicotinyl compound and a pyrethroid. WO2014152980 discloses a spot-on composition comprising a neonicotinoid compound and a pyrethroid. EP1585389 discloses termiticide compositions comprising acetamiprid and bifenthrin. EP1701616 discloses a method of controlling household pests comprising treatment using a mixture of acetamiprid and bifenthrin. Notwithstanding the enhanced activity enabled by such combination of actives, increased toxicity of the composition to the user remains a key concern in commercial utilization of the combination. Several attempts (largely unsuccessful) have been made in the past to significantly reduce the mammalian toxicity levels of the combination. Concerns are largely focused on acute oral, dermal and inhalation toxicity of the combination. There is, therefore, a need to have a composition of acetamiprid and bifenthrin having low toxicity to the user.

OBJECTS OF THE INVENTION

One object of the invention is to provide a composition of acetamiprid and bifenthrin that has low levels of toxicity.

Another object of the invention is to provide a composition of acetamiprid and bifenthrin having a toxicity falling in category III or above in OECD GHS 2013 classification.

Another object of the invention is to provide a method for control of insects and acarids using a composition comprising acetamiprid, bifenthrin and a toxicity control agent.

A further object of the invention is to provide a method for preparing granules comprising a toxicity control agent and acetamiprid and bifenthrin as the active ingredients.

SUMMARY OF INVENTION

In one aspect, the invention provides a composition comprising
 a) Acetamiprid
 b) Bifenthrin and
 c) a toxicity control agent In another aspect, the invention provides a composition of acetamiprid, bifenthrin and a toxicity control agent wherein the toxicity control agent is present in such an amount as to render the composition a toxicity falling in category III or above in OECD GHS 2013 classification.

In another aspect, the invention provides a composition of acetamiprid, bifenthrin and a toxicity control agent wherein the toxicity control agent is a mixture of a lignin sulfonic acid salt and castor oil ethoxylate.

In another aspect, the invention provides a composition of acetamiprid, bifenthrin and a toxicity control agent wherein ratio by weight of castor oil ethoxylate to lignin sulfonic acid salt is in the range of 1:4 to 1:20.

In another aspect, the invention provides a composition of acetamiprid, bifenthrin and a toxicity control agent wherein the composition comprises acetamiprid and bifenthrin in a ratio by weight of 1:1.

In another aspect, the invention provides a composition comprising acetamiprid, bifenthrin and a toxicity control agent wherein the composition is a granular composition.

In one aspect, the invention provides a method for control of insects and acarids, the method comprising treating a plant, a plant propagation material or a harvested plant material with a composition comprising acetamiprid, bifenthrin and a toxicity control agent.

In one aspect, the invention provides a method for control of insects and acarids, the method comprising treating a plant, a plant propagation material or a harvested plant material with a composition comprising acetamiprid, bifenthrin and a toxicity control agent wherein the insects are selected from the group consisting of *Bemisia Tabaci, A. gossypii* and *Anthonomus grandis*.

In one aspect, the invention provides a method for control of insects and acarids, the method comprising treating a plant, a plant propagation material or a harvested plant material with a composition comprising acetamiprid, bifenthrin and a toxicity control agent wherein the plant is a soybean or cotton plant.

In a still further aspect, the invention provides a method for preparing granules comprising acetamiprid and bifenthrin as the active ingredients, the method comprising preparing a dough comprising the active ingredients and a toxicity control agent, granulating the dough at a temperature less than 50° C. and drying the granules in a fluidized bed dryer.

DETAILED DESCRIPTION

The present inventors have been successful in preparing a composition of acetamiprid and bifenthrin that has low levels of toxicity. The present invention provides a composition comprising acetamiprid, bifenthrin and a toxicity control agent.

The toxicity control agent of the composition of the present invention is typically a mixture of a lignin sulfonic acid salt and a castor oil ethoxylate. Advantageously, the lignin sulfonic acid salt is selected from the group consisting of sodium lignosulfonate and calcium lignosulfonate. The toxicity control agent is present in such an amount as to render the composition a toxicity falling in category III or above in OECD GHS 2013 classification. Typically, the ratio by weight of castor oil ethoxylate to lignin sulfonic acid salt in the toxicity control agent of the composition is in the range of 1:4 to 1:20. Though the active ingredients (acetamiprid and bifenthrin) in the composition of the present invention can be combined in different ratios by weight, usually a ratio by weight of 1:1 is preferred. In addition to the active ingredients and the toxicity control agent, the composition of the invention can contain other ingredients customarily used in preparing an agrochemical composition. Various such ingredients include adjuvants, de-foamers, carriers and wetting agents. The wetting agents that can be used in preparing the composition of this invention include both nonionic and anionic wetting agents. The anionic wetting agents that can be used include sulfated fatty alcohols, sulfated olefins, sulfated amide condensates, alkyl-aryl polyether sulfates, alkyl sulfonates, sulfonated amides, sulfonated ethers and alkyl-aryl sulfonates. The nonionic wetting agents that can be used in preparing the composition of the present invention include fatty acid-alkanolamine condensates, ethylene oxide adducts of fatty acids, ethylene oxide adducts of fatty alcohols, alkyl-aryl polyether alcohols and polypropylene glycol-ethylene oxide condensates. Advantageously, the wetting agent used in preparing the composition of the present invention is sodium lauryl sulfate. The composition of the present invention can be formulated into water dispersible granules, wettable powder, dry flowable or dust. Advantageously, the composition is formulated as water dispersible granules. The process of manufacture of the water dispersible granules involve various steps including mixing, grinding, dough making, extrusion, drying and sieving. Mixing is usually performed in a blender. Grinding involve micronizing a mixture of ingredients using an air jet mill. Typically, the granules are dried in a fluidized bed dryer. To ensure that highly dispersible granules are obtained, care is taken while preparing the dough, extruding and drying not to exceed a temperature of 50° C. The high dispersibility of the composition of the present invention ensures that the composition is easily applied in the field without choking of the applicator. The composition of the present invention can be used for treating plant, a plant propagation material or a harvested plant material. Advantageously, the composition of the present invention is used for foliar application of a plant. The composition of the present invention is very effective in, but not limited to, controlling insects such as sucking pests (whitefly, aphids, brown stink bug), caterpillar and boll weevil. Further, the composition of the present invention is effective against insects on various crops including, but not limited to, soybean and cotton.

The composition of the present invention has low levels of toxicity. Low toxicity of the composition was confirmed by mammalian studies performed on wistar rats, rabbits as well as on guinea pigs. The result of these studies is displayed in table I.

TABLE 1

Mammalian toxicity studies of Acetamiprid + Bifenthrin composition

| Test | Toxicity category (OECD GHS 2013) |
|---|---|
| Acute Oral | Category III |
| Acute Dermal | Category 5 |
| Acute inhalation | Category 5 |
| Acute Dermal irritation | Category IV |
| Acute eye irritation | Not classified as an eye irritant |
| Skin sensitisation | Not considered as positive |

As evident from table I, the composition of the present invention has low levels of toxicity. Oral toxicity of the composition falls in category III of OECD GHS 2013 classification. This indicates low levels of oral toxicity of the composition. Further, acute dermal as well as acute inhalation toxicity of the composition of the present invention falls in category 5 of OECD GHS 2013 classification, thus indicating significantly low dermal and inhalation toxicity. Furthermore, as evident from results displayed in table I, the composition of the present invention is not classified either as an eye irritant or for skin sensitivity as per OECD GHS 2013 classification, further confirming the low toxicity of the composition. Furthermore, acute dermal irritation for the composition of the present invention also falls under category IV of the OECD GHS 2013 classification. It may be noted that being a solid composition used as an insecticide, the most critical parameters of toxicity of the composition of the present invention, from the point of view of a user, are acute dermal, acute inhalation, acute dermal irritation and eye irritation. As evident from table 1, for all these parameters, the composition of the present invention falls in highly safe category. In contrast, the commercially available solid formulation of a combination of Acetamiprid and Bifenthrin, namely, Transport® Termiticide insecticide, though non-irritant to skin, is classified as an eye irritant, has an $LC_{50}$ value for inhalation toxicity of >0.51 mg/l in a 4 hour study on rats as compared to $LC_{50}$ value for inhalation toxicity of >5.184 mg/l in a 4 hour study on rats for the composition of the present invention.

The present invention is further illustrated by way of the following non-limiting examples.

EXAMPLES

Example 1: Preparation of Low Toxicity Acetamiprid+Bifenthrin Composition

Acetamiprid (25% by weight) and Bifenthrin (25% by weight) were mixed with a toxicity control agent comprising calcium lignosulfonate (4%), sodium lignosulfonate (14%) and castor oil ethoxylate (1%) in a blender. Appropriate amounts of aluminium silicate (carrier) and defoamer were added and the mixture was blended until a homogeneous mixture was obtained. The mixture was then micronized using an air jet mill. A dough was prepared by adding appropriate amount of water and the dough was kneaded in a kneader. Granulation was carried out in an extruder keeping the temperature of the mixture less than 50° C. Granules were then dried in a fluidized bed dryer.

Example 2: Mammalian Studies of Toxicity of the Composition on Wistar Rats, Rabbits and Guinea Pigs Acute oral toxicity study (Up and Down Procedure) was conducted (following OECD 425 and OCSPP 870.1100 protocol) with 8-11 weeks old female wistar rats that were given a single oral dose of the composition prepared as in example 1. The main test was conducted with an initial dose-level of 175 mg composition per kilogram weight in one animal. Subsequently, additional female wistar rats received doses of 550, 175 and 55 mg per kilogram body weight according to the Up and Down procedure.

In acute dermal toxicity study (following OECD 402 and OCSPP 870.1200 protocol), a group of 10 to 12 weeks old wistar rats (5 males and 5 females) were dermally exposed to the composition prepared as in example 1 for 24 hours following application at a limit dose of 2000 mg/kg body weight. The required amount (434.0 to 583.80 mg) of the composition (pulverized and moistened with RO water) was applied over the clipped area (approximately 7×5 cm body surface area) and the rats were observed over a period of 14 days.

In an acute inhalation toxicity study (following OECD 403 and OCSPP 870.1300 protocol), 5 male and 5 female rats (8 to 9 weeks old) were exposed to breathing zone concentration of 5.184 mg of the composition prepared as in example 1 per liter of air using a nose-only inhalation exposure system. The rats were exposed for 4 hours followed by a 14 day post-exposure period.

In an acute dermal irritation study (following OECD 404 and OCSPP 870.2500 protocol), 3 adult male New Zealand white rabbits were dermally exposed to 500 mg of the composition of the present invention (pulverized and moistened with 0.5 ml of distilled water), for 4 h (applied to approximately 6 cm$^2$ area of skin). Initially one rabbit was tested with a single patch applied evenly to the intact skin for a period of 4 h. Based on the observations at 24 h post patch removal, two additional rabbits were tested simultaneously to confirm the irritation response. The control skin site of each rabbit was untreated. The treated and control sites were covered with a gauze patch that was secured at the margins by non-irritating tape for a period of 4 h. At the end of 4 h exposure period, the residual test item was removed with cotton soaked in distilled water. The skin reactions of each rabbit were observed at 1, 24, 48, and 72 h post patch removal. Irritation was scored according to OECD 404.

In an acute eye irritation study (following OECD 405 and OCSPP 870.2400 protocol), 3 adult female New Zealand white rabbits were given a single ocular application of 0.1 mL of the composition prepared as in example 1 in right eye of the rabbit while the contralateral eye remained untreated and served as the control. Initially, one rabbit was tested. Based on the results obtained in 24 h post-test item application (TIA), the irritation response was confirmed by testing two additional rabbits simultaneously. Observations were made at 1, 24, 48 and 72 hours post TIA.

Skin sensitization study was performed (following OECD 406 and OCSPP 870.2600 protocol) on thirty Hartley strain guinea pigs randomly divided into two groups. The control group comprised 10 guinea pigs (5 males and 5 females) and the treatment group comprised 20 guinea pigs (10 males and 10 females). Based on the results of the pilot study, 100 mg of the composition prepared as in example 1 was moistened with 0.2 mL of distilled water and was selected for topical induction applications (days 0, 7 and 14) and challenge exposure on day 28.

Results of the toxicity studies performed as in example 2 are displayed in table 1. Having understood the low mammalian toxicity of the composition of the present invention, the composition was further evaluated for its ability to control insects. Studies were conducted on control of insects such as whitefly (*bemisia tabaci*), aphid (*A. gossypii*) and boll weevil (*Anthonomus grandis*). The composition was applied over the field by way of randomized block treatments with repetitions. Effectiveness of treatment was evaluated at intervals (7 days after first or second application and 10 days after 3$^{rd}$ application) by counting the number of adult insects. For effective comparison, dosage of application determined for the composition of the present invention as well as for comparative (commercial) samples is the equilibrium dosage (at which a composition displays control of a particular insect in such a manner that the control is invariant to dosage). The results of this study are displayed in table 2.

From table 2, it is quite clear that the composition of the present invention is superior in control of adult whitefly (*Bemisia tabaci*), adult aphids (*A. gossypii*) and boll weevil (*Anthonomus grandis*).

The high efficiency (80% and 87.5% respectively) of control of whitefly on soybean crops achieved by using the composition of the present invention as compared to the efficiency (68% and 73%) of control achieved by using commercial samples (of Galil® SC) is a clear indicator of the higher efficiency of whitefly control using the composition of the present invention.

Further, the relatively higher control of adult aphids and boll weevil (87.8% and 92.0%) on cotton achieved by the composition of the present invention as compared to the control (31.3% and 80.0%) achieved by using commercial samples (of Marshal® SC and Capture® EC) clearly affirms the superior efficiency of insect control using the composition of the present invention.

TABLE 2

Comparative study of control of insects using the composition of the present invention and commercial insecticide samples

| Insect | Crop studied | Days after application | Concentration of active ingredients (A + B) (g L$^{-1}$) | Dosage of application Lha$^{-1}$ | Efficiency (%) of control using composition of present invention | Efficiency (%) of control using commercial sample |
|---|---|---|---|---|---|---|
| Bemisia Tabaci (adults) | Soybean | 7 days (after first application) | 250 + 250 | 0.180 | 80.0 | 68.0 (Galil ® SC† - −0.3 Lha$^{-1}$) |
| Bemisia Tabaci (adults) | Soybean | 7 days (after second application) | 250 + 250 | 0.180 | 87.5 | 73.4 (Galil ® SC† - 0.3 Lha$^{-1}$) |
| A gossypii (adults) | Cotton | 7 days (after first application) | 250 + 250 | 0.120 | 87.8 | 31.3 (Marshal ® 400 SC†† - 0.3 Lha$^{-1}$) |
| Anthonomus grandis (adults) | Cotton | 10 days (after third application) | 250 + 250 | 0.180 | 92.0 | 80.0 (Capture ® 400 EC††† - 0.15 Lha$^{-1}$) |

†Imidacloprid 250 + Bifenthrin 50
††Carbosulfan 400
†††Bifenthrin 400

The present invention provides a safe and environmentally benign composition of acetamiprid and bifenthrin. By selecting a combination of lignin sulfonic salt(s) and castor oil ethoxylate, the inventors of the present invention have been successful in arriving at a solution to a long standing technical problem of toxicity in a combination of insecticidal actives, viz., acetamiprid and bifenthrin. Such low toxicity compositions of insecticidal actives are very much desired due to the increasing safety concerns the compositions have on the health and well-being of the user. Interestingly, the low toxicity composition of the present invention has superior efficiency of control of insects in soybean and cotton fields as compared to the commercially available insecticides. An insecticidal composition that has low mammalian toxicity while having high efficiency of control of insects is quite unique and is a technical advance over the prior art.

The above description is illustrative only and is not limiting. The present invention is defined by the claims that follow and their full range of equivalents.

The invention claimed is:

1. A composition comprising:
   a) acetamiprid,
   b) bifenthrin, and
   c) a toxicity controlling agent, wherein the toxicity controlling agent is a mixture of a lignin sulfonic acid salt and castor oil ethoxylate,
   wherein the composition has a toxicity falling in category III or above in GHS 2013 classification.

2. The composition according to claim 1, wherein ratio by weight of castor oil ethoxylate to lignin sulfonic acid salt is in the range of 1:4 to 1:20.

3. The composition according to claim 1, wherein the composition comprises acetamiprid and bifenthrin in a ratio by weight of 1:1.

4. The composition according to claim 1, wherein the composition is a granular composition.

5. A method for controlling insects and acarids, the method comprising: treating a plant, a plant propagation material, or a harvested plant material with a composition according to claim 1.

6. The method according to claim 5, wherein the insects are selected from the group consisting of *Bemisia Tabaci, A. gossypii* and *Anthonomus grandis*.

7. The method according to claim 5, wherein the plant is a soybean plant or a cotton plant.

8. A method for preparing a composition according to claim 1, the method comprising:
   (i) preparing a dough comprising acetamiprid and bifenthrin and the toxicity controlling agent,
   (ii) granulating the dough obtained in step (i) at a temperature less than 50° C., and
   (iii) drying the granules in a fluidized bed dryer.

9. The method of claim 8, wherein the toxicity controlling agent comprises calcium lignosulfonate, sodium lignosulfonate, and castor oil ethoxylate.

* * * * *

UNITED STATES PATENT AND TRADEMARK OFFICE
CERTIFICATE OF CORRECTION

PATENT NO.         : 10,172,348 B2
APPLICATION NO.    : 15/482515
DATED              : January 8, 2019
INVENTOR(S)        : Paresh Vithaldas Talati et al.

It is certified that error appears in the above-identified patent and that said Letters Patent is hereby corrected as shown below:

On the Title Page

In Column 1, Line 14, above "(51) Int. Cl." insert -- Foreign Application Priority Data
Jun. 30, 2016 (IN)........................ 201631022544 -- as a new field entry.

Signed and Sealed this
Eighteenth Day of August, 2020

Andrei Iancu
*Director of the United States Patent and Trademark Office*